United States Patent [19]  [11] Patent Number: 4,745,191
Husbands  [45] Date of Patent: May 17, 1988

[54] 1-((A-SUBSTITUTED PHENYL-ω-SUBSTITUTED PIPERAZINYL)ALKENYL) CYCLOHEXANOL

[75] Inventor: G. E. Morris Husbands, Berwyn, Pa.

[73] Assignee: American Home Products Corporation, New York, N.Y.

[21] Appl. No.: 103,223

[22] Filed: Sep. 30, 1987

[51] Int. Cl.⁴ ............... C07D 403/04; C07D 295/08; A61K 31/505; A61K 31/495
[52] U.S. Cl. ........................ 544/295; 544/357; 544/397
[58] Field of Search .............. 544/295, 357, 397

[56] References Cited

U.S. PATENT DOCUMENTS 3,192,112  6/1965  Biel ........................ 544/397
3,435,036  3/1969  Regnier et al. ............ 544/295
4,675,319  6/1987  Nardi et al. .............. 544/357

FOREIGN PATENT DOCUMENTS

38726/85  2/1985  Australia .

Primary Examiner—Glennon H. Hollrah
Assistant Examiner—James H. Turnipseed
Attorney, Agent, or Firm—Richard K. Jackson

[57] ABSTRACT

The compounds

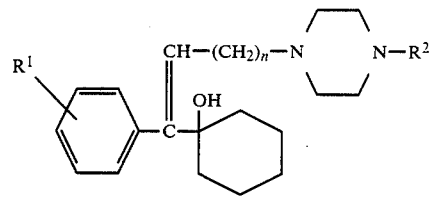

in which $R^1$ is 3-hydroxy, 4-hydroxy, 3-methoxy, 4-methoxy or 3,4-methylenedioxy; n is 1 or 2; and $R^2$ is

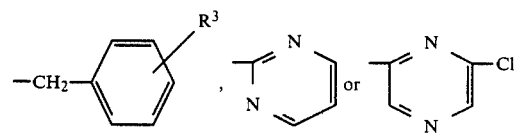

where $R^3$ is hydrogen, alkoxy of 1 to 6 carbon atoms, halo or trifluoromethyl; or a pharmaceutically acceptable salt thereof possess anxiolytic and antidepressant activity and are useful in treating psychiatric disorders involving anxiety and/or depression.

11 Claims, No Drawings

1-((A-SUBSTITUTED PHENYL-ω-SUBSTITUTED PIPERAZINYL)ALKENYL) CYCLOHEXANOL

BACKGROUND OF THE INVENTION

Australian Patent Application No. 38726/85 discloses a group of antidepressant agents which includes the compound 1-(1-hydroxy-1-cyclohexyl)-3-dimethylamino-1-phenyl-1-propene (Example 65).

DESCRIPTION OF THE INVENTION

In accordance with this invention there is provided a group of 1-[(α-substituted phenyl-ω-substituted piperazinyl)alkenyl]cyclohexanol derivatives which possess mixed anxiolytic-antidepressant activities and in a few instances, a moderate level of antipsychotic activity. The compounds of this invention are embraced by the following structural formula:

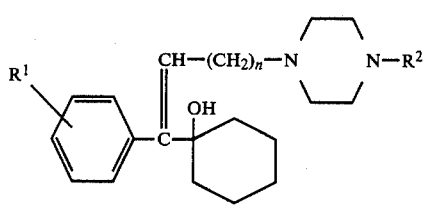

in which $R^1$ is 3-hydroxy, 4-hydroxy, 3-methoxy, 4-methoxy or 3,4-methylenedioxy;

n is 1 or 2; and $R^2$ is

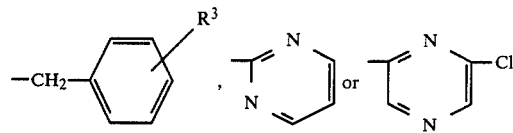

where $R^3$ is hydrogen, alkoxy of 1 to 6 carbon atoms, halo or trifluoromethyl;

or a pharmaceutically acceptable salt thereof.

In these compounds, the halo groups include chloro, bromo, iodo and fluoro substituents and the pharmaceutically acceptable salts of the basic compounds of this invention are formed conventionally by reaction of the free base with an equivalent amount of any acid which forms a non-toxic salt. Illustrative acids are either inorganic or organic, including hydrochloric, hydrobromic, fumaric, maleic, succinic, sulfuric, phosphoric, tartaric, acetic, citric, oxalic and similar acids. For parenteral administration, the use of water soluble salts is preferred, while either the free base or the pharmaceutically acceptable salts are applicable for oral administration.

The compounds of this invention are prepared by conventional methods. In general, the compounds in which n is equal to one are efficiently obtained by the following procedure:

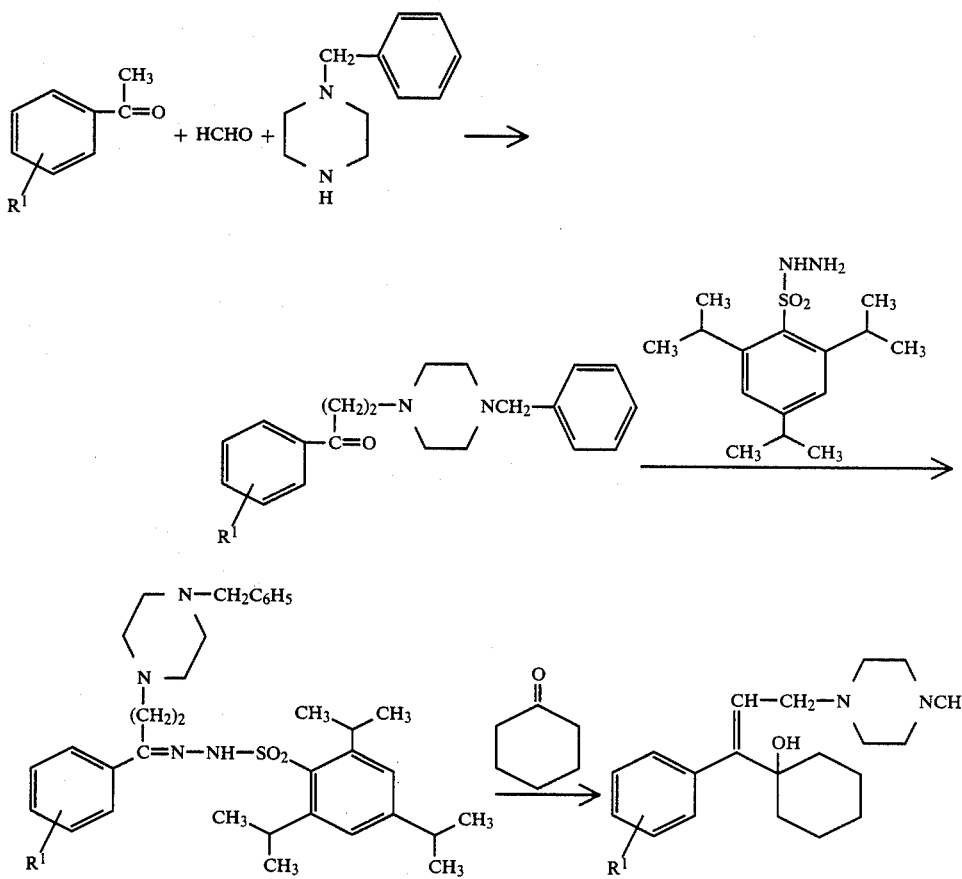

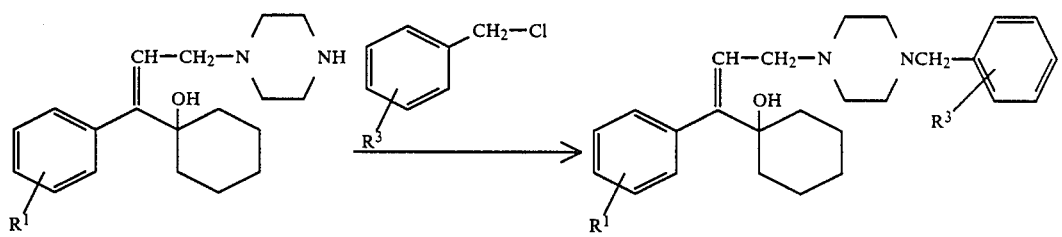

Alternatively, the intermediate piperazinobutyro or propio-phenones in which n is either 1 or 2 may be readily prepared by the following reaction:

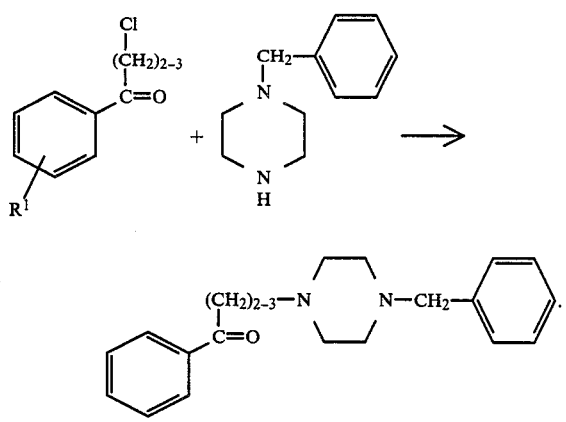

The reaction product, obtained from either process, is converted to the trisisopropylbenzenesulfonylhydrazone using the Bond modification of the Shapiro reaction [A. R. Chamberlain, J. E. Stemke and F. T. Bond, J. Org. Chem. 43, 147 (1978)]. The hydrazone yields a vinyl anion which condenses with cyclohexanone to form the cyclohexanol. Debenzylation is achieved via a catalytic hydrogenation over Pd/C catalyst. The products are purified using column chromatography and the secondary amine re-benzylated using appropriately substituted benzyl halides. Demethylation of the 3-methoxy or 4-methoxyphenyl derivatives with boron tribromide (BBr$_3$) as a final preparative step provides the hydroxyl substituted products. The N-benzyl intermediates are themselves final products in the invention.

The following examples illustrate the preparative techniques employed in the production of the compounds of the invention.

EXAMPLE 1

1-[1-(3-methoxyphenyl)-3-[4-(phenylmethyl)-1-piperazinyl]-1-propenyl]cyclohexanol A mixture of 3-methoxyacetophenone (53.8 g, 0.35 mole), paraformaldehyde (12.6 g), 1-benzylpiperazine dihydrochloride (106.2 g, 0.43 mole), ethanol (560 mL) and concentrated HCl (1.05 mL) was stirred and refluxed for 16 hours. The reaction mixture was cooled in ice and 1-(3-methoxyphenyl)-3-[4-(phenylmethyl)-1-piperazinyl]-1-propanone was separated. The dihydrochloride was filtered using ice-cold ethanol, washed with diethyl ether and dried in a desiccator under vacuum. Yield 50.8 g, m.p. 256°–259° C.

Elemental Analysis for: $C_{21}H_{26}N_2O_2.2HCl$ Calculated: C, 61.31; H, 6.86; N, 6.81. Found: C, 61.25; H, 6.99; N, 6.89.

To a suspension of 2,4,6-tris-isopropylbenzenesulfonylhydrazide (30 g, 0.01 mole) in a mixture of methanol (80 mL), diethyl ether (70 mL) and 5N isopropanolic HCl (30 mL) was added 1-(3-methoxyphenyl)-3-[4-(phenylmethyl)-1-propanone, dihydrochloride (42 g, 0.1 mole) and water (45 mL). The mixture was stirred at room temperature for 16 hours. The solid precipitate was filtered, washed with ethyl acetate and air dried. The free base was obtained as follows: the solid was partitioned between ethyl acetate and 4N NaOH solution (800 mL; 1:1 v/v). The phases were separated. The aqueous phase was extracted with ethyl acetate and the combined organic phase washed with brine, dried over magnesium sulfate and evaporated. The solid residue of 2,4,6-tris-(1-methylethyl)benzenesulfonic acid [1-(3-methoxyphenyl)-3-[4-(phenylmethyl)-1-piperazinyl]propylidene]hydrazide was washed and filtered with hexane and air dried, yield 42 g, m.p. 256°–259° C.

Elemental Analysis for: $C_{36}H_{50}N_4O_3S.\frac{1}{2}H_2O$ Calculated: C, 69.20; H, 8.12; N, 8.97. Found: C, 69.30; H, 7.98; N, 8.85.

2,4,6-Tris(1-methylethyl)benzenesulfonic acid [1-(3-methoxyphenyl)-3-[4-(phenylmethyl)-1-piperazinyl]-propylidene]hydrazide (42 g, 0.068 mole) was dissolved in dimethoxyethane (575 mL) under nitrogen with stirring. The solution was cooled to $-78°$ C. and N-butyllithium (78 mL, 2.5 moles) was added dropwise. The mixture was allowed to warm to 0° C. and was stirred at this temperature for 15 minutes, during which time the reaction mixture became dark brown in color. The mixture was cooled to $-50°$ C. and excess cyclohexanone (11.5 mL) added. The reaction mixture was stirred for 1½ hours during which time the color dissipated as the reaction approached ambient temperature. The mixture was poured into a diethyl ether-N HCl mixture (400 mL; 1:1 v/v). The phases were separated. The aqueous phase was extracted with diethyl ether and the organic phase with N HCl. The combined aqueous (acidic) phase was basified with solid KOH and extracted twice with ethyl acetate. The extract was washed with brine, dried over magnesium sulfate and evaporated to an amorphous solid. Wt. 14 g. The product was dissolved in diethyl ether and the solution treated with excess 4N-isopropanolic HCl. The dihydrochloride of the title compound was obtained, m.p. 230°–232° C.

Elemental Analysis for: $C_{27}H_{36}N_2O_2.2HCl.H_2O$ Calculated: C, 63.39; H, 7.88; N, 5.48. Found: C, 63.35; H, 7.78; N, 5.81.

EXAMPLE 2

1-[1-(4-methoxyphenyl)-3-[4-(phenylmethyl)-1-piperazinyl]-1-propenyl]cyclohexanol By replacing 2,4,6-tris(1-methylethyl)benzenesulfonic acid [1-(3-methoxyphenyl)-3-[4-(phenylmethyl)-1-piperazinyl]propylidene]hydrazide in Example 1 with a molar equivalent amount of 2,4,6-tris(1-methylethyl)benzenesulfonic acid [1-(4-methoxyphenyl)-3-[4-(phenylmethyl)-1-piperazinyl]propylidene]hydrazide and following the procedure described therein, 1-[1-(4-methoxyphenyl)-3-[4-(phenylmethyl)-1-piperazinyl]-1-propenyl]cyclohexanol was obtained in 80% yield. The product was converted to the dihydrochloride using 4N-isopropanolic HCl, m.p. 214°–216° C., yield 42%.

Elemental Analysis for: $C_{27}H_{30}N_2O_2.2HCl$ Calculated: C, 65.71; H, 7.76; N, 5.68. Found: c, 65.41; H, 7.39; N, 5.79.

EXAMPLE 3

1-[1-(3-methoxyphenyl)-3-[4-[(3-methoxyphenyl)methyl]-1-piperazinyl]-1-propenyl]cyclohexanol A solution of 1-[1-(3-methoxyphenyl)-3-(4-(phenylmethyl)-1-piperazinyl)-1-propenyl]cyclohexanol dihydrochloride (8.5 g, 17 mmole) in ethanol (200 mL) was hydrogenated in a Parr apparatus over 10% Pd/C (0.8 g) for five days. The catalyst was filtered and the filtrate evaporated. The residue was dissolved in 4N-NaOH (200 mL) and the mixture extracted with ethyl acetate (2×100 mL). The combined extract was washed with brine, dried over MgSO4 and evaporated to an oil. Wt. 4.1 g. The product, 1-[1-(3-methoxyphenyl)-3-(1-piprazinyl)-1-propenyl]cyclohexanol, was purified by column chromatography on silica gel with 10% methanol in chloroform yielding 1.4 g of pure product.

3-Methoxybenzyl chloride (1.28 g, 7.5 mol) and Cs2CO3 (5.9 g, 18 mmole) were added to a solution of 1-[1-(3-methoxyphenyl)-3-(1-piperazinyl)-1-propenyl]cyclohexanol (2.0 g, 6 mmole) in DMF (50 mL) and the mixture stirred at room temperature for one hour. Triethylamine (0.25 mL) was then added and the reaction mixture stirred overnight. The solvent was evaporated and the residue dissolved in chloroform. The solution was washed with water and the water back-extracted with chloroform. The combined organic solution was washed with brine, dried over magnesium sulfate and evaporated. The product was purified using column chromatography with chloroform as eluent and the purified title compound was converted to the hydrochloride. Yield 530 mg, m.p. 169°–171° C.

EXAMPLE 4

1-[3-[4-[[(3-chlorophenyl)methyl]-1-piperazinyl]-1-(3-methoxyphenyl)-1-propenyl]cyclohexanol By replacing 3-methoxybenzyl chloride with a molar equivalent of 3-chlorobenzyl chloride in Example 3, and following the procedure described therein, the title compound was obtained as the dihydrochloride, monohydrate salt, m.p. 230°–232° C. Yield: 30%.

Elemental Analysis for: $C_{27}H_{35}N_2O_2Cl.2HCl.H_2O$ Calculated: C, 59.40; H, 4.20; N, 5.13. Found: C, 59.61; H, 7.08; N, 5.09.

EXAMPLE 5

1-[3-[4-[(4-chlorophenyl)methyl]-1-piperazinyl]-1-(3-methoxyphenyl)-1-propenyl]cyclohexanol By replacing 3-methoxybenzyl chloride with a molar equivalent of 4-chlorobenzyl chloride in Example 3, and following the procedure described therein, the title compound was obtained as the dihydrochloride, hemihydrate, m.p. 243°–245° C. Yield 28%.

Elemental Analysis for: $C_{27}H_{35}N_2O_2Cl.2HCl.\frac{1}{2}H_2O$ Calculated: C, 60.39; H, 7.13; N, 5.22. Found: C, 60.03; H, 7.14; N, 5.21.

EXAMPLE 6

1-[1-(3-methoxyphenyl)-3-[4-[[4-(trifluoromethyl)phenyl]methyl]-1-piperazinyl]-1-propenyl]cyclohexanol By replacing 3-methoxybenzyl chloride with a molar equivalent of 4-trifluoromethylbenzyl chloride in Example 3, the title compound was obtained as the hydrochloride, hemihydrate, m.p. 188°–190° C. Yield 29%.

Elemental Analysis for: $C_{28}H_{35}N_2F_3.2HCl.\frac{1}{2}H_2O$ Calculated: C, 58.95; H, 6.71; N, 4.91. Found: C, 59.02; H, 6.65; N, 4.69.

EXAMPLE 7

1-[1-(3-methoxyphenyl)-3-[4-(2-pyridinyl)-1-piperazinyl]-1-propenyl]cyclohexanol By replacing 3-methoxybenzyl chloride in Example 3 with a molar equivalent amount of 2-chloropyrimidine, the title compound was obtained as the dihydrochloride, hemihydrate salt, m.p. 174°–176° C. Yield 22%.

Elemental Analysis for: $C_{24}H_{32}N_4O_2.2HCl.1\frac{1}{2}H_2O$ Calculated: C, 58.77; H, 7.19; N, 11.42. Found: C, 58.16; H, 6.99; N, 11.84.

Mass spectral analysis: Molecular weight 490 (M+1)+ by C.I.M.S.

EXAMPLE 8

1-[3-[4-(6-chloro-2-pyrazinyl)-1-piperazinyl]-1-(3-methoxyphenyl)-1-(3-methoxyphenyl)-1-propenyl]cyclohexanol By replacing 3-methoxybenzyl chloride in Example 3 with a molar equivalent amount of 2,6-dichloropyrazine and following the procedure described therein, the title compound was obtained. The product was converted to its fumarate salt via an acetone-diethyl ether solution, m.p. 145°–147° C. Yield: 34%.

Elemental Analysis for: $C_{24}H_{31}N_4O_2Cl.C_4H_4O_4$ Calculated: C, 60.16; H, 6.31; N, 10.02. Found: C, 60.43; H, 6.20; N, 9.53.

EXAMPLE 9

1-[1-(4-methoxyphenyl)-3-[4-[[4-(trifluoromethyl)phenyl]methyl]-1-piperazinyl]-1-propenyl]cyclohexanol Debenzylation of the product of Example 2 provides the intermediate which, like the corresponding 3-methoxyphenyl substituted compounds may be re-benzylated to tailor that group as desired. Debenzylation of the 4-methoxyphenyl derivative was performed as follows:

1-[1-(4-methoxyphenyl)-3-(4-phenylmethyl)-piperazinyl]-1-propenyl]cyclohexanol, dihydrochloride (5 g, 10.1 mmole) was dissolved in ethanol (225 mL) and was hydrogenated in a Parr apparatus over 5% Pd/C (0.5 g) for 72 hours. The catalyst was filtered and the filtrate evaporated. The residue was partitioned between ethyl acetate and 4N NaOH. The layers were separated. The aqueous layer was extracted with ethyl acetate and the combined organic solution was washed with brine, dried over MgSO$_4$ and evaporated. The oil obtained was chromatographed on silica gel using varying concentrations of methanol in chloroform. Yield of 1-[1-(4-methoxyphenyl)-3-(1-piperazinyl)-1-propenyl]-cyclohexanol was 1.8 g.

By replacing 1-[1-(3-methoxyphenyl)-3-(1-piperazinyl)-1-propenyl]cyclohexanol with a molar equivalent of 1-[1-(4-methoxyphenyl)-3-(1-piperazinyl)-1-propenyl]cyclohexanol in Example 6, the title compound was obtained. It was converted to the fumarate (1:2) salt, m.p. 222°–225° C. Yield: 23%

Elemental Analysis for: $C_{28}H_{35}N_2O_3F_3 \cdot 2C_4H_4O$ Calculated: C, 59.9; H, 6.01; N, 3.89. Found: C, 60.77; H, 6.13; N. 3.95.

EXAMPLE 10

1-[1-(4-methoxyphenyl)-4-[4-(phenylmethyl)-1-piperazinyl]-1-butenyl]cyclohexanol A mixture of γ-chloro-p-methoxybutyrophenone (45 g, 210 mole), 1-benzylpiperazine (35 mL, 200 mole) and anhydrous potassium carbonate (250 g) in methylisobutylketone (800 mL) was refluxed under nitrogen for 40 hours. The reaction mixture was cooled, poured into a beaker containing ice, then ethyl acetate was added. The layers were separated. The organic phase was washed with water, brine, dried over $K_2CO_3$ and evaporated to an oil. This residue was dissolved in diethyl ether (200 mL) and treated with excess 4N-isopropanolic HCl. The hydrochloride of 1-(4-methoxyphenyl)-4-[4-phenylmethyl)-1-piperazinyl]-1-butanone was obtained. Wt. 53 g. The product was converted to the free base with NaOH and purified by column chromatography. It was then converted to the dihydrochloride, m.p. 173°–175° C.

Elemental Analysis for: $C_{23}H_{28}N_2O_2 \cdot 2HCl \cdot 1\frac{1}{2}H_2O$ Calculated: C, 58.4; H, 6.69; N, 6.19. Found: C, 58.48; H, 7.09; N, 6.05.

By replacing 2,4,6-tris-(1-methylethyl)benzenesulfonic acid [1-(3-methoxyphenyl)-3-[4-(phenylmethyl)-1-piperazinyl]propylidene]hydrazide in Example 1 with 2,4,6-tris-(1-methylethyl)benzenesulfonic acid [1-(4-methoxyphenyl)-4-[4-(phenylmethyl)-1-piperazinyl]-butylidene]hydrazide and following the procedure described therein, the title compound was obtained. The product was dissolved in diethyl ether and treated with an isopropanolic solution of succinic acid (2 equivalents). The d-succinate was obtained in crystalline form, m.p. 146°–148° C. yield.

Elemental Analysis for: $C_{28}H_{38}N_2O_2 \cdot 2C_4H_6O_4$ Calculated: C, 64.46; H, 7.53; N, 4.17. Found: C, 64.11; H, 7.29; N, 4.30.

The antidepressant activity of the compounds of this invention was established by demonstrating their ability to inhibit synaptosomal uptake of norepinephrine ($^3$H-NE) and/or serotonin ($^{14}$C-5-HT) following the test procedure of Wood et al., J. Neurochem., 37 795 (1981).

The additional excellent anxiolytic property possessed by the compounds of this invention was established by demonstrating their strong affinity at 5-HT$_{1A}$ receptor binding sites through inhibition of [$^3$H] 8-hydroxy-2-(di-n-propylamino)tetraline binding at 5-HT binding sites in rat hippocamphal tissue, following the procedure of Hall et al., J. Neurochem., 44 1685 (1985).

Furthermore, as may be seen from the pharmacological data presented infra, some of the compounds embraced by the compound genus of this invention demonstrate marginal affinity for dopamine D$_2$ receptors, which is indicative of some element of limited antipsychotic activity [Seeman, Pharmacol. Rev. 32, 230 (1981)]. Examples of these compounds are those of Examples 1 and 4–6 demonstrating about 80% inhibition of $^3$H-haloperidol binding at D$_2$ receptors found in homogenized limbic brain tissue at 1 μM concentration of the test compound as determined in a modification of the test procedure of Fields et al., Brain Res., 136, 578 (1977) and Yamamura et al., eds., Neurotransmitter Receptor Binding, Raven Press, N.Y. (1978) as discussed in U.S. Pat. No. 4,636,563. The actual percentage reduction of $^3$H-haloperidol binding is reported infra and the larger the number, the greater the potential for dopamine D$_2$ receptor binding and antipsychotic activity.

The pharmacological test data obtained for a representative number of compounds of this invention in accordance with the standard experimental test procedures disclosed above appear in the following table:

| | Receptor Binding Ki (nM) or % Inhibition at 1 μM | | Neuronal Uptake IC$_{50}$ (μM) or % Inhibition at 10 μM | |
|---|---|---|---|---|
| Compound | 5HT$_{1A}$ | D$_2$ | NE | 5HT |
| Example 1 | 3 nM | 80% | 0.64 μM | 1.69 μM |
| Example 2 | 4 nM | 66% | 1.26 μM | 3.18 μM |
| Example 4 | 0.7 nM | 17 nM | 100% | 100% |
| Example 5 | 99% | 76% | | |
| Example 6 | 99% | 76% | | |
| Example 7 | 49 nM | 61% | 4.82 μM | 2.09 μM |
| Example 8 | 138 nM | | | |
| Example 10 | 74% | 53% | 0.19 μM | 0.92 μM |
| Buspirone | 10 nM 97%) | 84% (78 nM) | | |

In qualitatively evaluating the above data, high activity values in NE and 5-HT uptake correlate with antidepressant activity; high affinity values for 5-HT$_{1A}$ receptors (about 90% to 100%) correlate (by analogy with buspirone) with anxiolytic activity; high affinity values for D$_2$ receptor binding (greater than 80%) begin to show some antipsychotic activity.

From these data, the activity profile of the compounds of this invention are seen to be useful in the treatment of psychiatric disorders, in some instances, combining very desirable antidepressant-anxiolytic properties.

Hence, the compounds of this invention are antidepressant, anxiolytic agents useful in the treatment of depression and in alleviating anxiety. As such, they may be administered neat or with a pharmaceutical carrier to a patient in need thereof. The pharmaceutical carrier may be solid or liquid.

A solid carrier can include one or more substances which may also act as flavoring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both of pharmaceutically acceptable oils or fats. The liquid carrier can contain other suitable pharmaceutical additives such as solubilisers, emulsifiers, buffers, preservatives, sweeteners, flavoring agents, suspending agents, thickening agents, colors, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g., glycols) and their derivatives, and oils (e.g. fractionated coconut oil and arachis oil). For parenteral administration the carrier can also be an oil ester such as ethyl oleate and isopropyl myristate. Sterile liquid carriers are used in sterile liquid form compositions for parenteral administration. The liquid carrier for pressurised compositions can be halogenated hydrocarbon or other pharmaceutically acceptable propellent.

Liquid pharmaceutical compositions which are sterile solutions or suspensions can be utilized by, for example, intramuscular intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or table itself, or it can be the appropriate number of any such compositions in package form.

The dosage to be used in the treatment of anxiety or depression must be subjectively determined by the attending physician. The variables involved include the specific state of depression or anxiety and the size, age and response pattern of the patient.

What is claimed is:

1. A compound of the formula:

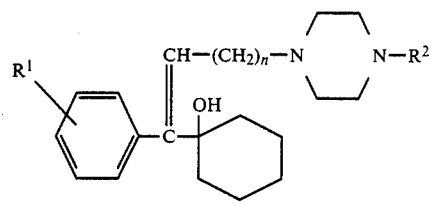

in which
$R^1$ is 3-hydroxy, 4-hydroxy, 3-methoxy, 4-methoxy or 3,4-methylenedioxy;
n is 1 or 2; and
$R^2$ is

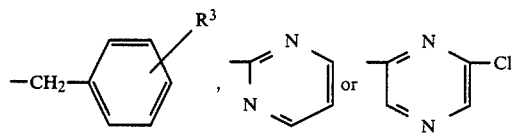

where $R^3$ is hydrogen, alkoxy of 1 to 6 carbon atoms, halo or trifluoromethyl;
or a pharmaceutically acceptable salt thereof.

2. The compound of claim 1 which is 1-[1-(3-methoxyphenyl)-3-[4-(phenylmethyl)-1-piperazinyl]-1-propenyl]cyclohexanol, or a pharmaceutically acceptable salt thereof.

3. The compound of claim 1 which is 1-[1-(4-methoxyphenyl)-3-[4-(phenylmethyl)-1-piperazinyl]-1-propenyl]cyclohexanol, or a pharmaceutically acceptable salt thereof.

4. The compound of claim 1 which is 1-[1-(3-methoxyphenyl)-3-[4-[(3-methoxyphenyl)methyl]-1-piperazinyl]-1-piperazinyl]-1-propenyl]cyclohexanol, or a pharmaceutically acceptable salt thereof.

5. The compound of claim 1 which is 1-[3-[4-[(3-chlorophenyl)methyl]-1-piperazinyl]-1-(3-methoxyphenyl)-1-propenyl]cyclohexanol, or a pharmaceutically acceptable salt thereof.

6. The compound of claim 1 which is 1-[3-[4-[(4-chlorophenyl)methyl]-1-piperazinyl]-1-(3-methoxyphenyl)-1-propenyl]cyclohexanol, or a pharmaceutically acceptable salt thereof.

7. The compound of claim 1 which is 1-[1-(3-methoxyphenyl)-3-[4-[[4-(trifluoromethyl)phenyl]methyl]-1-piperazinyl]-1-propenyl]cyclohexanol, or a pharmaceutically acceptable salt thereof.

8. The compound of claim 1 which is 1-[1-(3-methoxyphenyl)-3-[4-(2-pyrimidinyl)-1-piperazinyl]-1-propenyl]cyclohexanol, or a pharmaceutically acceptable salt thereof.

9. The compound of claim 1 which is 1-[3-[4-(6-chloro-2-pyrazinyl)-1-piperazinyl]-1-(3-methoxyphenyl)-1-(3-methoxyphenyl)-1-propenyl]cyclohexanol, or a pharmaceutically acceptable salt thereof.

10. The compound of claim 1 which is 1-[1-(4-methoxyphenyl)-3-[4-[[4-(trifluoromethyl)phenyl]methyl]-1-piperazinyl]-1-propenyl]cyclohexanol, or a pharmaceutically acceptable salt thereof.

11. The compound of claim 1 which is 1-[1-(4-methoxyphenyl)-4-[4-(phenylmethyl)-1-piperazinyl]-1-butenyl]cyclohexanol, or a pharmaceutically acceptable salt thereof.

* * * * *